US010245445B2

(12) United States Patent
Pyeon et al.

(10) Patent No.: US 10,245,445 B2
(45) Date of Patent: Apr. 2, 2019

(54) INFRARED-RAY LAMP TUBE

(71) Applicants: Chin-woong Pyeon, Busan (KR); Gyu-tae Pyon, Busan (KR); Yong-Joo Sin, Yongin-si, Gyeonggi-do (KR)

(72) Inventors: Chin-woong Pyeon, Busan (KR); Gyu-tae Pyon, Busan (KR)

(73) Assignees: Yong-Joo Sin, Yongin-si, Gyeonggi-Do (KR); Chin-Woong Pyeong, Busan (KR); Gyu-Tae Pyon, Busan (KR)

( * ) Notice: Subject to any disclaimer, the term of this patent is extended or adjusted under 35 U.S.C. 154(b) by 84 days.

(21) Appl. No.: 15/314,631

(22) PCT Filed: Jun. 30, 2015

(86) PCT No.: PCT/KR2015/006677
§ 371 (c)(1),
(2) Date: Nov. 29, 2016

(87) PCT Pub. No.: WO2016/010285
PCT Pub. Date: Jan. 21, 2016

(65) Prior Publication Data
US 2017/0189713 A1 Jul. 6, 2017

(30) Foreign Application Priority Data
Jul. 15, 2014 (KR) ........................ 10-2014-0088957

(51) Int. Cl.
*H01K 1/24* (2006.01)
*A61N 5/06* (2006.01)
*A61F 7/00* (2006.01)
*G02B 5/28* (2006.01)
*H01K 1/26* (2006.01)
*H01K 1/58* (2006.01)

(52) U.S. Cl.
CPC .............. *A61N 5/0625* (2013.01); *A61F 7/00* (2013.01); *G02B 5/281* (2013.01); *H01K 1/26* (2013.01); *H01K 1/58* (2013.01); *A61F 2007/0088* (2013.01); *A61N 2005/0654* (2013.01); *A61N 2005/0659* (2013.01); *A61N 2005/0665* (2013.01); *A61N 2005/0667* (2013.01)

(58) Field of Classification Search
CPC .......... A61N 5/0625; A61N 2005/0654; A61N 2005/0659; A61N 2005/0665; A61N 2005/0667
USPC .......................................................... 607/90
See application file for complete search history.

(56) References Cited

U.S. PATENT DOCUMENTS 5,200,124 A * 4/1993 Bowkett ................. B29C 35/08
 264/295
6,399,955 B1 * 6/2002 Fannon ..................... H01K 1/24
 250/424

* cited by examiner

*Primary Examiner* — Aaron F Roane
(74) *Attorney, Agent, or Firm* — Paratus Law Group, PLLC

(57) ABSTRACT

An infrared-ray lamp tube has; an elongate tube-shaped housing having an inner space defined therein, wherein the elongate tube-shaped housing have both side open ends; an infrared-ray emitting array disposed in the inner space, wherein an infrared-ray emitting array includes a plurality of halogen lamp units spacedly arranged in an array in the inner space in a length direction of the housing; two plugs respectively fitted into the both side open ends of the elongate tube-shaped housing; and a filtering liquid filling the inner space of the elongate tube-shaped housing.

4 Claims, 5 Drawing Sheets

[FIG. 1]
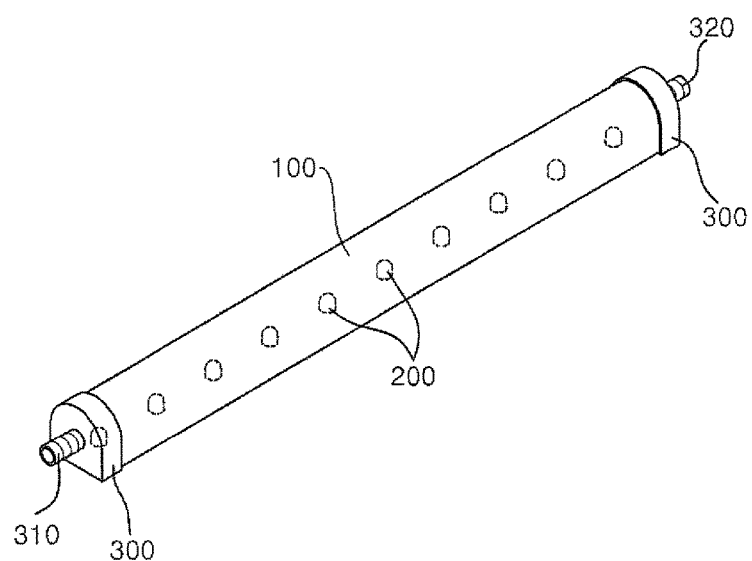

[FIG. 2]
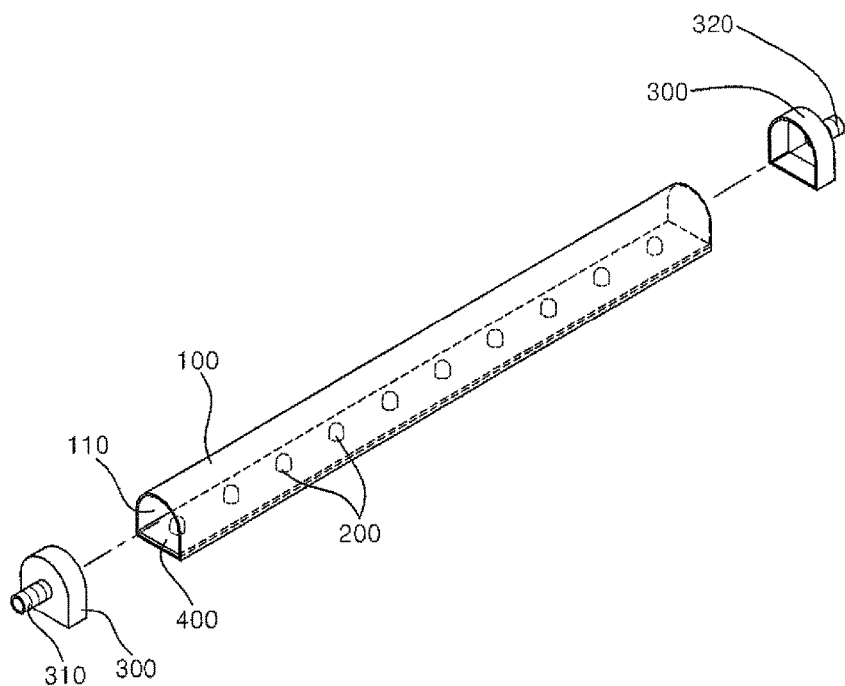
[FIG. 3]
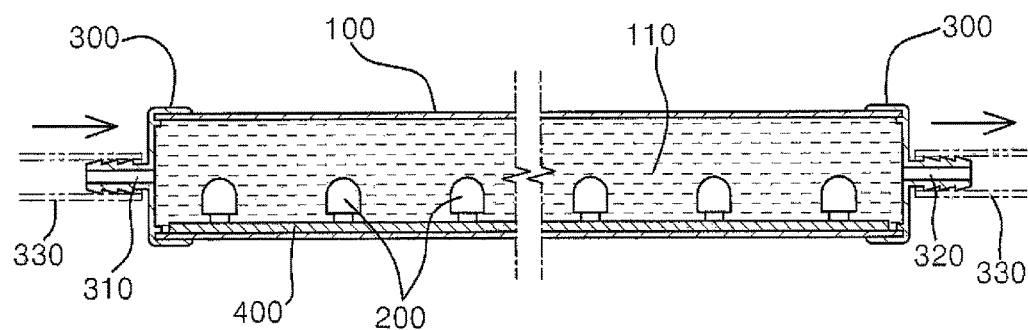

[FIG. 4]
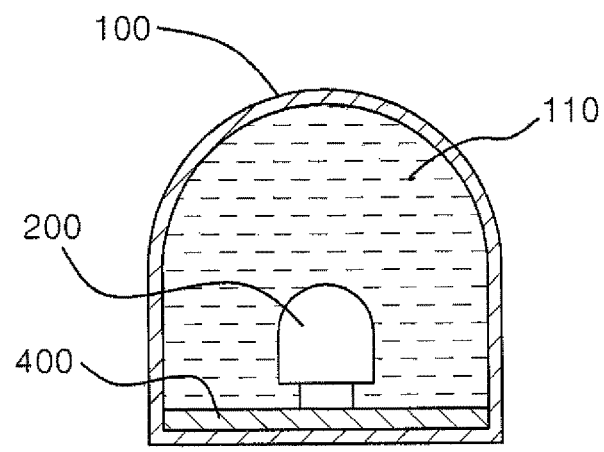
[FIG. 5]
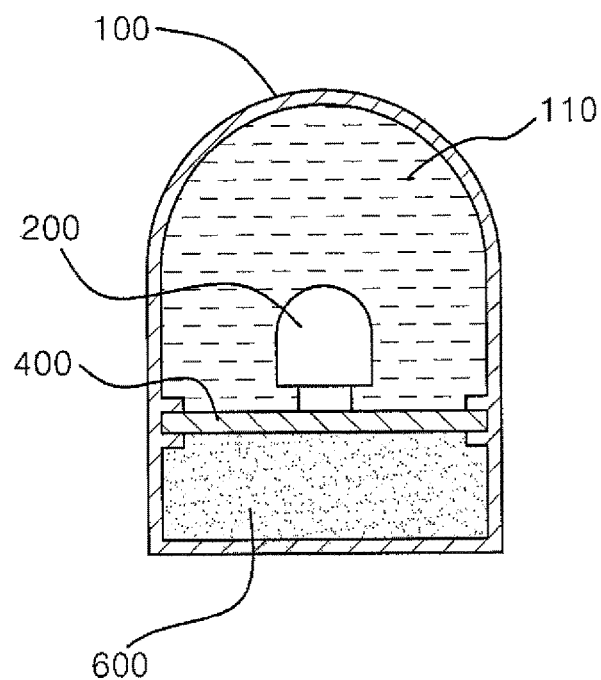

[FIG. 6]
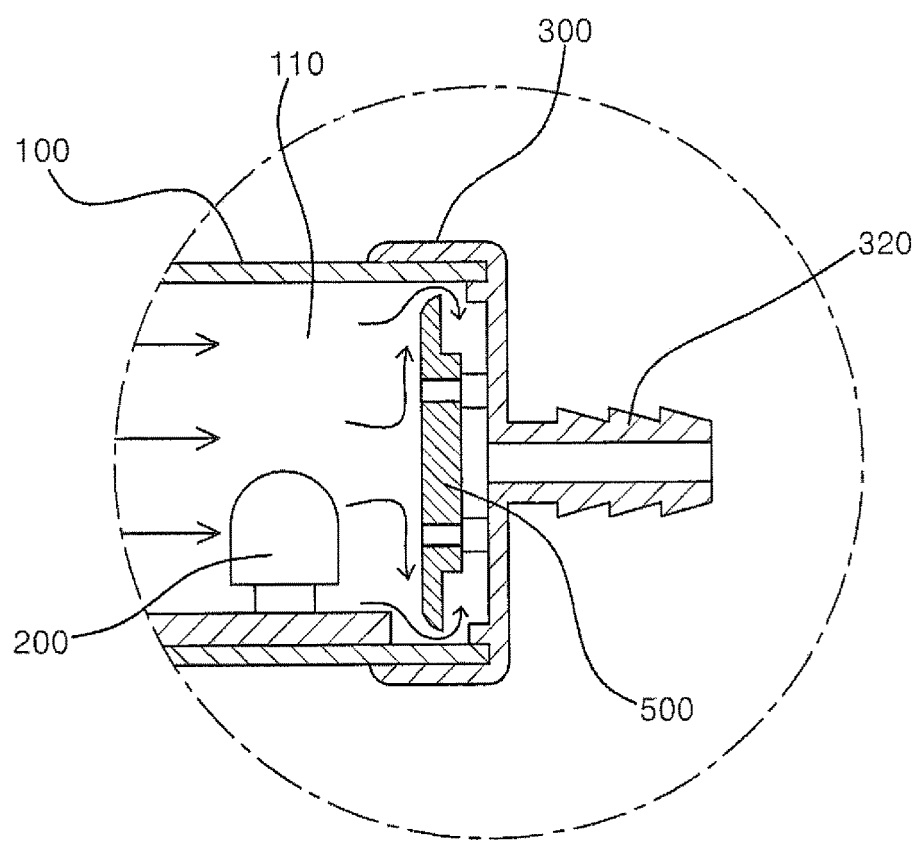

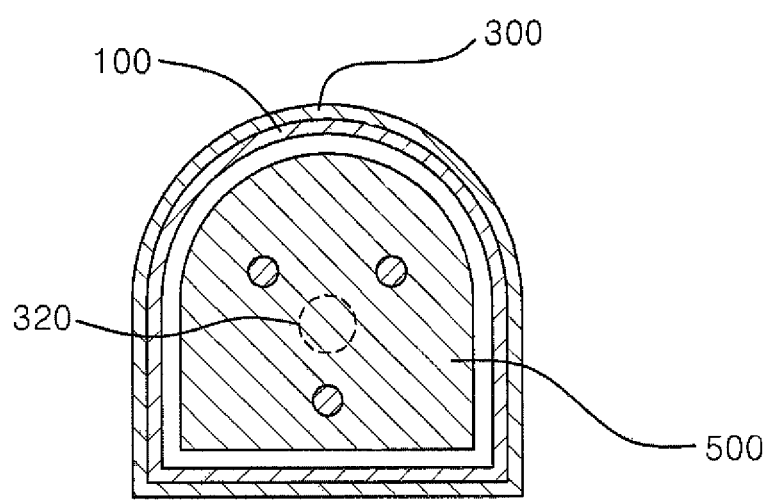
[FIG. 7]

INFRARED-RAY LAMP TUBE

CROSS-REFERENCE TO RELATED APPLICATION

This application claims the benefit of Korea patent application No. 10-2014-0088957 filed on Jul. 15, 2014, the entire content of which is incorporated herein by reference for all purposes as if fully set forth herein.

BACKGROUND

Field of the Present Disclosure

The present disclosure relates to an infrared-ray lamp tube, and, more particularly, to an infrared-ray lamp tube having an elongate tube-shaped housing receiving therein an infrared-ray emitting array and a filtering liquid, thereby to filter light beams of relatively longer wavelengths from the light beams emitted from the array.

Discussion of Related Art

An infrared rays penetrates into a 40 mm deep portion of the skin of human body to enlarge the blood vessels by promoting resonance, charging, and motion of molecules of the human cells, to make the blood circulation smooth, and to create self-heating. This increases a temperature of the inner deep portion of the body, strengthens metabolism, activates cellular tissue, promotes excretion of waste products, and relieves fatigue.

When the temperature of the deed potion of the human body increases, suppress of the proliferation of cancer cells and the activation of the immune system may be achieved. In other words, as the temperature of the deed potion of the human body increases, the proliferation of cancer cells is decreased and the immune system is activated. To be specific, the immune system is activated 5 to 6 times as the temperature of the deed potion of the human body increases by 1° C. The activity of the immune system decreases by about 40% as the temperature decreases by 1° C. at normal body temperature. Therefore, by increasing the temperature of the deed potion of the human body, cancer cells can be prevented from multiplying, and the immune system can be activated to ultimately reduce cancer cells.

Generally, the infrared ray lamp is not suitable for the treatment of hyperthermia because heat resulting from a high temperature is directly transmitted to the skin of the human body due to the long wavelength band of the infrared ray. Therefore, the infrared ray lamp has been limited to cooking apparatus, heating apparatus, and sterilizing apparatus. In some hospitals, the infrared ray lamp is used for physical therapies. Further, using the infrared-ray lamp, patients are getting burned by the strong heat resulting from the long-wavelength band of the infrared ray.

The prior art infrared-ray lamps are as follows:

Korean Utility Model Registration No. 421828 discloses an infrared-ray bulb device comprising an infrared-ray bulb connected to a socket base at the neck thereof and having a filament supported by a socket base and a molybdenum supporter in the bulb. The device includes a guide slot, a fixing slot, a guide projection, a stopper, and a constriction block.

The Korean patent No. 1051838 discloses an infrared lamp provided to radiate rays uniformly by reflecting heat, generated from a carbon fiber electrode, to an upper end of a quartz tube. A quartz tube is made of a material capable of projecting the light. The quartz tube makes an upper end be in parallel with a lower end. A carbon fiber electrode is installed within the quartz tube. The carbon fiber electrode receives current via an external terminal, connected to both ends of the quartz tube, and generates heat. A coating layer is formed in an upper end of the quartz tube. The coating layer reflects the heat to a lower part of the quartz tube when the heat from the carbon fiber electrode permeates an upper part of the quartz tube, so that the heat can be uniformly radiated under the quartz tube. Thermal balance can be realized without loss of the infrared ray.

The Korean patent No. 785551 discloses an IR (Infrared) lamp is provided to have directivity without an additional reflector, by coating a reflector on the surface of the lamp in a body. In a bar type IR lamp having a lamp and an infrared ray reflection coating layer, a reflection layer providing directivity of infrared ray radiation is formed on the surface of the lamp in a body. A part without the reflection layer is formed in a body with the coating layer. The coating layer is Au.

The Korean patent No. 317229 discloses an infrared-ray shield beam lamp wherein a filament is installed in a vacuum bulb, and a reflector is to reflect a light beam, and a fixing bar is fixed to a transparent insulation holder which fixes the infrared-ray divergent filament to the shield beam lamp, and an auxiliary reflection plate is fixed to the fixing bar and reflects the light from the filament to the reflector.

However, these prior arts are made up of a general infrared-ray lamp. The prior arts for efficiently irradiating the infrared ray through the reflection plate are proposed. There is no configuration to filter light beams of relatively longer wavelengths from the light beams emitted from the infrared-ray lamp. As a result, when used in a thermal therapy that directly irradiates a body with the infrared ray lamp in the prior art, the temperature of the skin surface irradiated with the infrared ray is elevated, but the temperature rise of the deep body portion may not be expected. The light-beams of the relatively longer wavelengths may cause a burn or blackening in the skin.

SUMMARY

The present disclose is to address the above-described challenges.

The present disclose is to provide an infrared-ray lamp tube having an elongate tube-shaped housing receiving therein an infrared-ray emitting array and a filtering liquid, thereby to filter light beams of relatively longer wavelengths from the light beams emitted from the array, then, to lead to the temperature rise of the deep body portion.

Further, the present disclose is to provide an infrared-ray lamp tube having an elongate tube-shaped housing receiving therein an infrared-ray emitting array and a filtering liquid, thereby to filter light beams of relatively longer wavelengths from the light beams emitted from the array, then, to suppress the burn or blackening in the skin.

Furthermore, the present disclose is to provide an infra-red-ray lamp tube to allow the circulation of the filtering liquid in the elongate tube-shaped housing, to effectively cool the filtering liquid and, thus, the infrared-ray emitting array.

In one aspect of the present disclosure, there is provided an infrared-ray lamp tube comprising; an elongate tube-shaped housing having an inner space defined therein, wherein the elongate tube-shaped housing have both side open ends; an infrared-ray emitting array disposed in the inner space, wherein an infrared-ray emitting array includes a plurality of halogen lamp units spacedly arranged in an array in the inner space in a length direction of the housing; two plugs respectively fitted into the both side open ends of the elongate tube-shaped housing; and a filtering liquid filling the inner space of the elongate tube-shaped housing.

In one implementation, one of the plugs has a filtering liquid inlet defined therein, and the other of the plugs has a filtering liquid outlet.

In one implementation, the elongate tube-shaped housing is made of a light-transmitting material to allow a light beam from the infrared-ray emitting array to pass through the housing, and the light-transmitting material includes a polycarbonate-based synthetic resin.

In one implementation, the infrared-ray lamp tube further comprises a reflection plate disposed in the elongate tube-shaped housing at a first inner side face thereof to reflect a light beam from the infrared-ray emitting array toward a second inner side face thereof, wherein the first side face is opposite to the second side face.

In one implementation, the infrared-ray lamp tube further comprises a bubble-discharge guide in the inner space of the elongate tube-shaped housing in an adjacent position to the filtering liquid outlet, wherein the bubble-discharge guide defines a gap between an inner wall face of the elongate tube-shaped housing and the guide.

In one implementation, the infrared-ray lamp tube further comprises an insulating filling disposed between the reflection plate and the first inner side face of the elongate tube-shaped housing.

In accordance with the present disclosure, the filtering liquid filters light beams of relatively longer wavelengths from the light beams emitted from the array, thereby to lead to the temperature rise of the deep body portion.

Further, in accordance with the present disclosure, the filtering liquid filters light beams of relatively longer wavelengths from the light beams emitted from the array, thereby to lead to suppress the burn or blackening in the skin. Furthermore, in accordance with the present disclosure, the circulation of the filtering liquid in the elongate tube-shaped housing may effectively cool the filtering liquid and, thus, the infrared-ray emitting array.

Furthermore, in accordance with the present disclosure, due to the bubble-discharge guide, the filtering liquid may only flow through the defined gap toward the filtering liquid outlet. Thus, the bubbles remaining on the side wall face of the elongate tube-shaped housing may be forcedly removed when the filtering liquid flows through the defined gap in a high speed. Thus, the filtering liquid may effectively filter the light beams of the relatively longer wavelengths from the light beams emitted from the light emitting array.

BRIEF DESCRIPTION OF THE DRAWINGS

FIG. 1 is a perspective view of an infrared-ray lamp tube in accordance with one embodiment of the present disclosure.

FIG. 2 is an exploded perspective view of an infrared-ray lamp tube in accordance with one embodiment of the present disclosure.

FIG. 3 is a front cross-sectional view of an infrared-ray lamp tube in accordance with one embodiment of the present disclosure.

FIG. 4 is a side cross-sectional view of an infrared-ray lamp tube in accordance with one embodiment of the present disclosure.

FIG. 5 is a side cross-sectional view of a configuration where a reflection plate is spaced from an inner face of the housing via an insulating filling.

FIG. 6 is a front cross-sectional view of a configuration where a bubble-discharge guide is coupled to the plug at the outlet.

FIG. 7 is a side cross-sectional view of a configuration where a bubble-discharge guide is coupled to the plug at the outlet.

DETAILED DESCRIPTIONS

Example embodiments will be described in more detail with reference to the accompanying drawings. The present disclosure, however, may be embodied in various different forms, and should not be construed as being limited to only the illustrated embodiments herein. Descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The present lamp may be installed to the interior wall of a sauna room, a sitting chair and a bed-type thermal therapy apparatus. It can be used in various forms. The present lamp may be installed in a vertical, horizontal, and diagonal or tilted orientation. The present disclosure is not limited thereto.

As shown in FIG. 1 to FIG. 3, the present infrared-ray lamp tube may include an elongate tube-shaped housing 100 having an inner space 110 defined therein, wherein the elongate tube-shaped housing 100 have both side open ends; an infrared-ray emitting array 200 disposed in the inner space 11, wherein an infrared-ray emitting array 200 includes a plurality of halogen lamp units spacedly arranged in an array in the inner space 110 in a length direction of the housing 100; two plugs 300 respectively fitted into the both side open ends of the elongate tube-shaped housing 100; and a filtering liquid filling the inner space 110 of the elongate tube-shaped housing 100.

The elongate tube-shaped housing 100 may be hollow, that is, may have the inner space 110 formed therein. The elongate tube-shaped housing 100 may be made of a light-transmitting material to allow a light beam from the infrared-ray emitting array 200 to pass through the housing 100. For example, the light-transmitting material may include a polycarbonate (PC)-based synthetic resin. The polycarbonate (PC)-based synthetic resin may have better shock resistance than a glass and good heat resistance.

The inner space 110 of the elongate tube-shaped housing 100 may be filled with the filtering liquid. The filtering liquid may be, for example, water. The filtering liquid may function to absorb light-beams of wavelengths equal or larger than 1300 nm from light-beams of wavelengths having 375 to 5000 nm emitted from the infrared-ray emitting array 200. Thus, only light-beams of wavelengths below 1300 nm may be irradiated from the present infrared-ray lamp tube. It is physically proven that the water functions to absorb light-beams of wavelengths equal or larger than 1300 nm. Further, it is well known that light-beams of wavelengths equal or larger than 1100 nm have very lower transmittance through the skin. Thus, most of light-beams of wavelengths of 1100 nm to 5000 nm may be absorbed into an outer portion of the skin to be poor at increasing a temperature of a target deep portion of the body. Further, light-beams of wavelengths of 1100 nm to 5000 nm may cause a burn in the skin.

The elongate tube-shaped housing 100 may have the both plugs 300 respectively fitted into the both side open ends of the elongate tube-shaped housing 100. The both plugs 300 may be respectively and fluid-tightly fitted into the both side open ends. To improve the fluid-tightness, each packing member may be fitted between each housing 100 end and each plug 300.

One of the plugs 300 has a filtering liquid inlet 310 defined therein, and the other of the plugs 300 has a filtering liquid outlet 320. This may allow a circulation of the filtering liquid. The filtering liquid inlet 310 and filtering liquid outlet 320 may be fluid-communicated with a circulation channel 330. A circulation pump (not shown) may be operatively coupled to the circulation channel 330 to enforce the circulation of the filtering liquid through the elongate tube-shaped housing 100. In this way, the heated present tube due to the heat generated from the infrared-ray emitting array 200 may be cooled. Thus, when the present tube is closer to the skin, the skin may not be uncomfortable due to the hot tube.

The infrared-ray emitting array 200 may include a plurality of halogen lamp units spacedly arranged in an array in the inner space 110 in a length direction of the housing 100. The halogen lamp unit may emit a near-infrared-ray. Further, a reflection plate 400 may be disposed in the elongate tube-shaped housing 100 at a first side face thereof to reflect the ray from the infrared-ray emitting array 200 toward a second side thereof, wherein the first side is opposite to the second side face.

In one example, the reflection plate 400 may directly contact the first side face of the elongate tube-shaped housing 100. In another example, as shown in FIG. 5, the reflection plate 400 may be spaced from the first side face of the elongate tube-shaped housing 100 via an insulating filling 600 disposed therebetween. In the insulating filling 600, an electrical wire may be disposed to supply a power to the infrared-ray emitting array 200. Thus, the electrical wire may be insulated from the filtering liquid.

The present infrared-ray lamp tube may be installed in a vertical, horizontal, or tilted orientation. When the present infrared-ray lamp tube may be installed in the horizontal or tilted orientation, the filtering liquid may not fully fill the inner space 110 of the elongate tube-shaped housing 100 through the filtering liquid inlet 310, and, thus, air bubbles may be formed in the liquid in the inner space 110 of the elongate tube-shaped housing 100. The air bubbles may remain a top portion of the elongate tube-shaped housing 100 adjacent to the filtering liquid outlet 320. The air bubbles may not be removed using the constant filtering liquid circulation, to deteriorate the light beam filtering effect of the filtering liquid.

In order to solve this problem, as shown in FIG. 6, a bubble-discharge guide 500 may be disposed in the inner space 110 of the elongate tube-shaped housing 100 in an adjacent position to the filtering liquid outlet 320. In one example, the bubble-discharge guide 500 may be integrated with the plug 300 at the filtering liquid outlet 320. In one example, the bubble-discharge guide 500 may be separated from the plug 300 at the filtering liquid outlet 320. In any case, the bubble-discharge guide 500 may define a gap between an inner wall face of elongate tube-shaped housing 100 and the guide 500. In one example, the bubble-discharge guide 500 may have a plate form having the same shape as the cross-sectional shape of the elongate tube-shaped housing 100. Thus, the filtering liquid may only flow through the defined gap toward the filtering liquid outlet 320. Thus, the bubbles remaining on the side wall face of the elongate tube-shaped housing 100 may be forcedly removed when the filtering liquid flows through the defined gap in a high speed.

In this way, the light-beams emitted from the infrared-ray emitting array 200 may be filter by the filtering liquid in the elongate tube-shaped housing 100 to be irradiated into a target portion of the body. In this connection, only light-beams of wavelengths below 1300 nm may be irradiated from the present infrared-ray lamp tube, to increase the temperature of a deep target portion of the body. At the same time, the light-beams of wavelengths of 1100 nm to 5000 nm causing a burn or blackening in the skin may be suppressed to be irradiated to the skin. Thus, this inhibits the proliferation of cancer cells and activates the immune system.

Examples of various embodiments are illustrated and described above. It will be understood that the description herein is not intended to limit the claims to the specific embodiments described. On the contrary, it is intended to cover alternatives, modifications, and equivalents as may be included within the spirit and scope of the present disclosure as defined by the appended claims.

What is claimed is:

1. An infrared-ray lamp tube comprising:
    an elongate tube-shaped housing having an inner space defined therein, wherein the elongate tube-shaped housing have both side open ends;
    an infrared-ray emitting array disposed in the inner space, wherein an infrared-ray emitting array includes a plurality of halogen lamp units spacedly arranged in an array in the inner space in a length direction of the elongate tube-shaped housing;
    a filtering liquid filling the inner space of the elongate tube-shaped housing;
    two plugs respectively fitted into the both side open ends of the elongate tube-shaped housing, and including:
        a first plug having an inlet through which the filtering liquid flows into the inner space; and
        a second plug opposite to the first plug and having an outlet through which the filter liquid in the inner space flows out; and
    a bubble-discharge guide in the inner space in a position adjacent to the outlet, and including:
        a front surface facing the first plug, and positioned to conceal the outlet when viewed from the first plug;
        an outer circumferential surface spaced apart from an inner surface of the elongate tube-shaped housing with a first gap; and
        a rear surface opposite to the front surface, facing the outlet, and spaced apart from an inner wall of the second plug with a second gap being in fluid communication with the first gap such that the filtering liquid in the inner space flows toward the outlet over the front surface through the first pap and the second gap in order.

2. The infrared-ray lamp tube of claim 1, wherein the elongate tube-shaped housing is made of a light-transmitting material to allow a light beam from the infrared-ray emitting array to pass through the elongate tube-shaped housing, and the light-transmitting material includes a polycarbonate-based synthetic resin.

3. The infrared-ray lamp tube of claim 1, further comprising a reflection plate, disposed in the elongate tube-shaped housing at a first inner side face thereof to reflect a light beam from the infrared-ray emitting array toward a second inner side face thereof, wherein the first side face is opposite to the second side face.

4. The infrared-ray lamp tube of claim 3, further comprising an insulating filling disposed between the reflection plate and the first inner side face of the elongate tube-shaped housing.

* * * * *